US00PP16470P3

(12) United States Plant Patent
Lintott

(10) Patent No.: US PP16,470 P3
(45) Date of Patent: Apr. 25, 2006

(54) ***CHRYSANTHEMUM* PLANT NAMED 'STARLET WHITE'**

(50) Latin Name: *Chrysanthemum morifolium*
Varietal Denomination: Starlet White

(75) Inventor: Keith G. Lintott, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 253 days.

(21) Appl. No.: 10/693,738

(22) Filed: Oct. 24, 2003

(65) Prior Publication Data

US 2004/0083520 P1 Apr. 29, 2004

Related U.S. Application Data

(60) Provisional application No. 60/421,386, filed on Oct. 25, 2002.

(51) Int. Cl.
*A01H 5/00* (2006.01)

(52) U.S. Cl. ..... Plt./294

(58) Field of Classification Search ..... Plt./294
See application file for complete search history.

(56) References Cited

U.S. PATENT DOCUMENTS

PP10,218 P 1/1998 Pieters ..... Plt./294

OTHER PUBLICATIONS

Royal Van Zanten Garden Mum Catalog 2002 listing *Chrysanthemum* variety 'Starlet White' at pp. 5 (color picture), 9 and 14.

*Primary Examiner*—Anne Marie Grunberg
*Assistant Examiner*—June Hwu
(74) *Attorney, Agent, or Firm*—Howrey Simon Arnold & White LLP

(57) ABSTRACT

A new variety of *Chrysanthemum* plant named 'Starlet White,' having a good uniform canopy of small white single flowers. The new variety has medium vigor, a free branching and uniform spreading habit, and good foliage presentation.

1 Drawing Sheet

Latin name of the genus and species: Botanical classification: *Chrysanthemum morifolium.*

Variety denomination: The new *Chrysanthemum* variety denomination is 'Starlet White.'

BACKGROUND OF THE INVENTION

The present invention comprises a new and distinct cultivar of *Chrysanthemum* botanically known as *Chrysanthemum morifolium*, and referred to by the cultivar name 'Starlet White.'

'Starlet White,' identified as 30450-0, originated from a cross made in a controlled breeding program in Chichester, West Sussex, United Kingdom. The female parent of the new variety is the unpatented variety known as 'Leyla.' The male parent of the new variety is the variety known as 'Pidoul' (U.S. Plant Pat. No. 10,218).

The new variety 'Starlet White' has been asexually reproduced by vegetative cuttings in Chichester, West Sussex, United Kingdom and the distinguishing characteristics are retained through successive generations of asexual reproduction.

BRIEF SUMMARY OF THE INVENTION

'Starlet White' is a garden type of *Chrysanthemum* plant variety having a uniform domed and round shape carrying many small white single flowers.

Comparison With Female Parent

Plants of the new *Chrysanthemum* variety 'Starlet White' are similar to the female parent variety 'Leyla' in plant habitat and growth rate. In side-by-side comparisons in Chichester, West Sussex, United Kingdom, under commercial practice, plants of the new *Chrysanthemum* variety 'Starlet White' differed from plants of the parent 'Leyla' in the following characteristics.

1. The new variety 'Starlet White' produces white flowers whereas the parent 'Leyla' produces yellow flowers.
2. Plants of the new variety 'Starlet White' have smaller and shorter inflorescence than plants of the parent 'Leyla.'

Comparison With Male Parent

Plants of the new *Chrysanthemum* variety 'Starlet White' are similar to the male parent 'Pidoul' in plant habit and growth rate. However, in side-by-side comparisons in Chichester, West Sussex, United Kingdom, under commercial practice, plants of the new *Chrysanthemum* variety 'Starlet White' differed from plants of the parent 'Pidoul' in the following characteristics.

1. The new variety 'Starlet White' has smaller white single flowers than the parent variety 'Pidoul.'
2. Plants of the new variety 'Starlet White' have less flowers than the parent variety 'Pidoul.'
3. Plants of the new variety 'Starlet White' are less vigorous than plants of the parent variety 'Pidoul.'

Comparison With Other Varieties

Plants of the new *Chrysanthemum* variety 'Starlet White' are similar to the unpatented variety 'Tightrope' in plant habit and growth rate. However, in side-by-side comparisons in Chichester, West Sussex, United Kingdom, under commercial practice, plants of the new *Chrysanthemum* variety 'Starlet White' differed from plants of 'Tightrope' in the following characteristics.

1. The new variety 'Starlet White' has smaller white single flowers than the variety 'Tightrope.'
2. Plants of the new variety 'Starlet White' have more flowers than the variety 'Tightrope.'
3. Plants of the new variety 'Starlet White' are less vigorous than plants of the variety 'Tightrope.'

BRIEF DESCRIPTION OF ILLUSTRATION

Typical specimens of the plant and flowers for the new *Chrysanthemum* variety 'Starlet White' are shown in the accompanying digital photograph. The colors shown are as true as possible within the usual limits of this kind of illustration.

FIG. 1 is a whole plant view of the new variety 'Starlet White' grown in a pot.

The plant shown in the illustration is 63 days from the commencement of planting outdoors in mid-June.

DETAILED BOTANICAL DESCRIPTION

The following description of the new *Chrysanthemum* variety 'Starlet White' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 65° F. to 75° F. during the day under natural light conditions. The plants were grown outdoors in mid-June in 4 liter pots using loamless compost. No growth retardants were used. To produce a commercial product the plants may be pinched once with the center bud removed. The typical container size for commercial growth is 4 liter. It has been observed that the shelf life of the new variety is about 25 days with a response time of about 9 weeks natural season. The new variety is suitable for growth in a temperature range of 50° F. to 75° F.

The new variety may be produced as a pot plant. The following description is with respect to a plant produced as garden pot plant. In the description of this new *Chrysanthemum* variety, color values have been taken from The Royal Horticultural Society Colour Chart (R.H.S.C.C.).

Plant

Plant type: Pot.
Habit: Domed — Round.
Height: 45 cm.
Width: 45 cm.
Branching characteristics: Free Branching and Spreading.
Length of lateral branches: 15–26 cm.
Number of breaks from pinch: 9–11.
Stem color: Near 137B.
Response time: 63 days natural season.
Vigor: Medium — Medium/Short.
Shelf life: 25 days.
Disease (susceptibility/resistance observed): None observed to date.
Pest (susceptibility/resistance observed): None observed to date.
Growth retardant type and treatment: No treatment necessary.

The plants were grown for 9 weeks in natural season conditions.

Propagation:
*Type.*—Vegetative Propagation via Stem Cuttings.
*Time to rooting.*—12 days with soil temperatures of 70° F.
*Rooting habit.*—Fine and Fibrous.

Foliage

Number of leaves per lateral branch: 10–12.
Compound or single: Single.
Arrangement of leaves: Alternate.
*Shape of leaf.*—Typically 5 lobed ovate.
*Size of leaf.*—Width (cm): 2.5–3 Length (cm): 3–4.5.
*Leaf apex.*—Acute.
*Base.*—Cordate.
*Attachment.*—Petioled.
*Aspect.*—Slightly Undulating.
*Margin.*—Palmately Lobed.
*Surface characteristics.*—Top: Slightly Pubescent. Bottom: Slightly Pubescent.
Petiole:
*Color.*—Near 138B.
*Length.*—1.5–2 cm.
*Diameter.*—0.2–0.4 cm.
Venation: Net prominent mid vein at underside.
*Color.*—Upper side: near 144B. Under side: Near 144B.
Color: Mature Leaf, upper side: near 138A; under side: near 138B. Young Leaf, upper side: Near 138A; under side: near 138B.

Flower

Flower appearance: Matte.
Flower type: Single.
Flower form: Flat/Slightly Cupped.
Flower shape: Round.
Flowering habit: Cyme.
Number of blossoms per branch: 11–20.
Inflorescence form: Corymibiform in form, in that the outer stalks are longer than the inner stalks, but flowering habit is cyme from the terminal flower first.
Depth of fully expanded blossoms: 1 cm.
Diameter of fully expanded blossoms: 3.5 cm.
Phyllaries:
*Number.*—23–25.
*Color.*—Near 137C.
*Length.*—5–8 mm.
*Width.*—1–2 mm.
*Texture/appearance.*—Shiny/Slightly Pubescent.
Pedicel:
*Length.*—Terminal: 5 cm; lateral: 9 cm.
*Color.*—Near 137C.
*Surface.*—Slightly pubescent.
*Habit.*—Slightly Curving.
*Strength.*—Moderately strong.
Peduncle:
*Length.*—11–19 cm.
*Diameter.*—0.2–0.6 cm.
*Color.*—Near 137C.
*Surface.*—Slightly pubescent.
*Strength.*—Moderately strong.
Ray florets:
*Form/shape.*—Straight with oblong shape.
*Texture/appearance.*—Matte.

*Number per flower.*—48–50.
*Length.*—1.5–1.8 cm; Width: 4–5 mm.
*Apex.*—Rounded.
*Base.*—Tubular.
*Margin.*—Entire.

Disc florets:
*Form/shape.*—Cylindrical.
*Texture/appearance.*—Shiny.
*Number per flower.*—120–150.
*Length.*—7 mm; Width: 1 mm.
*Diameter of disc.*—1 cm.

Fragrance: None.

Flower bud (at onset of color):
*Length.*—8 mm.
*Diameter.*—8 mm.
*Form/shape.*—Globular.

General flower color:
1. *Ray florets, upper side.*—Immature: near 158D. Mature: near 155D. Older/Fading: 155D.
2. *Ray florets, under side.*—Immature: near 158D. Mature: near 155D. Older/Fading: near 155D.
3. *Disc florets.*—Immature: near 17B. Mature: near 22A. Older/Fading: near 22A.
4. *Bud.*—20C.

Flower progression with age: Flowers develop a pale pink color with age and become slightly cupped.

Lastingness of blooms: Near 25 days.

Reproductive Organs

Gynoecium present on ray and disc florets:

Ray florets per individual flower:
*Pistil number.*—25–30 observed.
*Stigma color.*—Near 144D.
*Stigma shape.*—Forked.
*Style color.*—Near 144D.
*Style length.*—1–2 mm.

Disc florets per individual flower:
*Pistil number.*—120–150 observed.
*Stigma color.*—Near 144D.
*Stigma shape.*—Forked.
*Style color.*—Near 144D.
*Style length.*—2 mm.

Androecium present on disc florets only:
*Stamen number.*—40–50 observed.
*Anther shape.*—Ovoid.
*Anther color.*—Near 14C.
*Pollen color.*—Near 12A.
*Pollen quantity.*—Medium.

Fruit and seeds: None observed.

What is claimed is:

1. A new and distinct variety of *Chrysanthemum* plant, substantially as described and illustrated herein.

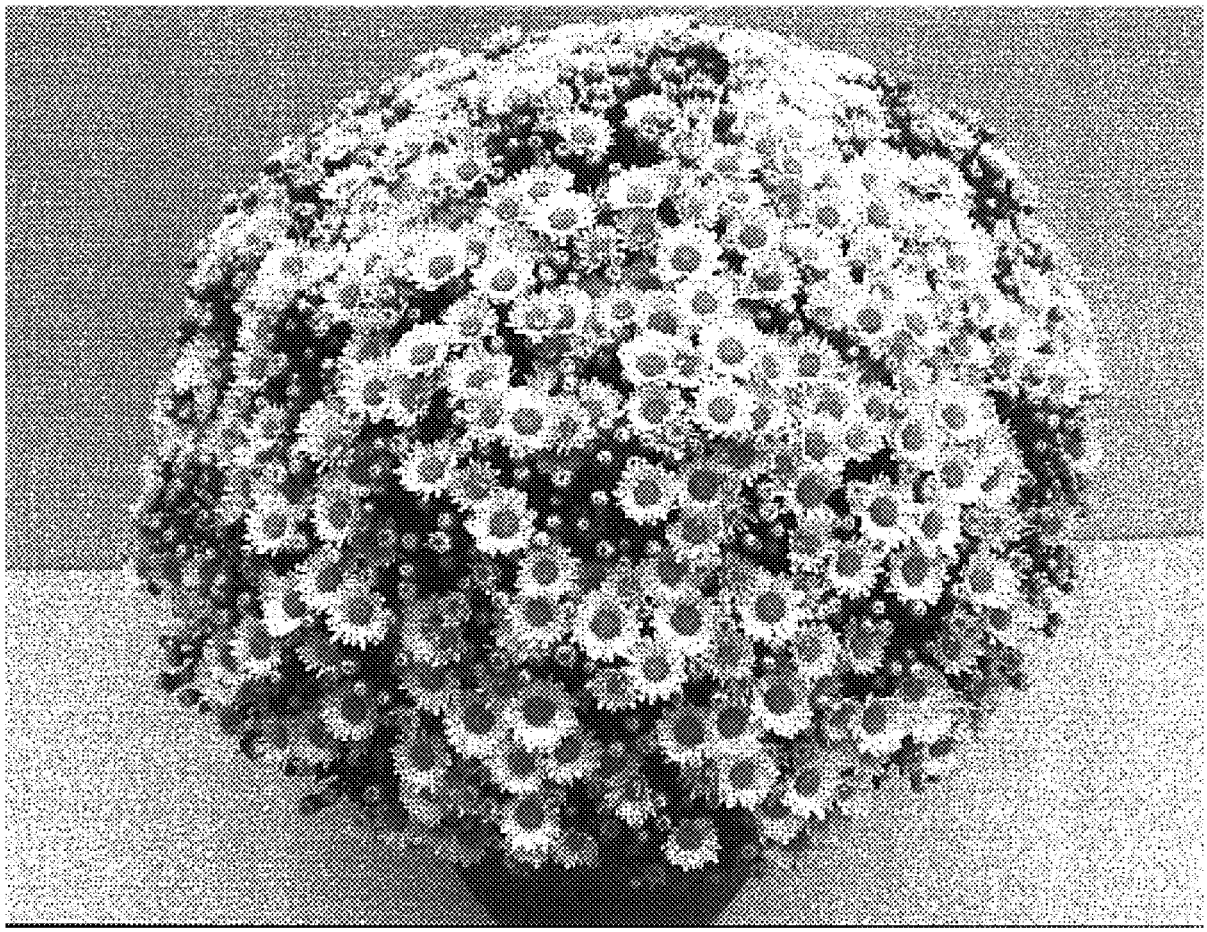

* * * * *